United States Patent

Hawkins et al.

Patent Number: 6,133,432
Date of Patent: Oct. 17, 2000

[54] PROCESSES FOR PREPARING PESTICIDAL INTERMEDIATES

[75] Inventors: David William Hawkins; David Alan Roberts; John Harry Wilkinson, all of Ongar, United Kingdom; Jean-Louis Clavel, Ampuis, France

[73] Assignee: Rhone-Poulenc Agro, Lyons, France

[21] Appl. No.: 09/142,074

[22] PCT Filed: Mar. 3, 1997

[86] PCT No.: PCT/EP97/01036

§ 371 Date: Dec. 1, 1998

§ 102(e) Date: Dec. 1, 1998

[87] PCT Pub. No.: WO97/32843

PCT Pub. Date: Sep. 12, 1997

[30] Foreign Application Priority Data

Mar. 5, 1996 [GB] United Kingdom .................... 9604691

[51] Int. Cl.[7] .......................... C09B 79/00; C09B 29/42; C07D 231/02; C07D 231/04; C07C 253/00

[52] U.S. Cl. .................. 534/885; 548/364.1; 548/371.7; 558/332; 546/275.4; 534/770; 534/771; 534/581

[58] Field of Search ...................................... 534/581, 770, 534/771, 885; 548/371.7; 558/332; 546/275.4

[56] References Cited

U.S. PATENT DOCUMENTS 5,232,940   8/1993   Hatton et al. ............................ 514/407
5,451,598   9/1995   Salmon et al. .......................... 314/404

FOREIGN PATENT DOCUMENTS 0234119   9/1987   European Pat. Off. .
0295117   12/1988  European Pat. Off. .
93/06089   4/1993   WIPO .
94/21606   9/1994   WIPO .

OTHER PUBLICATIONS

Smith et al, *J. Am. Chem. Soc.*, 71, pp. 3418–3419 (1949).
Whiteley et al, *Synthesis*, pp. 392–394 (1978).
Higson et al, *J. Chem. Soc.* 89, pp. 1455–1472 (1906).
Dickinson et al, *J. Am. Chem. Soc.* 82, pp. 6132–6136 (1960).

*Primary Examiner*—Joseph McKane
*Assistant Examiner*—Joseph Murray
*Attorney, Agent, or Firm*—Burns, Doane, Swecker & Mathis, L.L.P.

[57] ABSTRACT

A process for preparing a compound of the formula

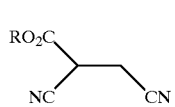

(I)

wherein R is $C_1$–$C_{18}$ alkyl by reacting a compound of the formula $$RO_2C\text{—}CH_2CN \quad (II)$$

with a cyanide salt and formaldehyde or source thereof. Compounds of formula (I) are useful intermediates to pesticidally active compounds.

38 Claims, No Drawings

PROCESSES FOR PREPARING PESTICIDAL INTERMEDIATES

The instant Application is A 371 of PCT/EP97/01036 filed on Mar. 3, 1997.

This invention relates to a process for preparing certain cyanomethylpropane derivatives and the use of these compounds in the synthesis of pesticides and pesticide intermediates.

Ethyl 2,3-dicyanopropionate was first prepared and characterised by Higson and Thorpe (J.Chem.Soc. 89, 1460 (1906)) who obtained the material in good yield (70–81%) by reaction of formaldehyde cyanohydrin with the sodium salt of ethyl cyanoacetate. Dickinson {J. Am. Chem. Soc. 82, 6132 (1960)} repeated this work. This method of preparing the dicyanopropionate suffers from a significant drawback in that it is first necessary to isolate the intermediate formaldehyde cyanohydrin. This highly water soluble cyanohydrin is obtained by lengthy continuous extraction and has a limited stability, often decomposing violently upon attempted distillation. Furthermore, this reaction requires care given the risk of formation of dimeric side-products. The preparation of dicyanopropionates has also been described by Whiteley and Marianelli (Synthesis (1978), 392) with the process leading to 2,3-disubstituted succinodinitriles from the cyanoacetate, an aldehyde (a 1 to 3 carbon alkylaldehyde or benzaldehyde) and potassium cyanide via 3-substituted-2,3- dicyanopropionates (which were not isolated). However, the yield decreases dramatically from isobutyraldehyde to acetaldehyde. In the same manner Smith and Horwitz (J. Am. Chem. Soc. 1949, 71, 3418) described the same reaction with a ketone with a yield of 70%. This prior art therefore teaches that yields improve with increasing size of group adjacent to the carbonyl group.

In one aspect the present invention seeks to provide a process for preparing cyanomethyl propane derivatives satisfying one or more of the following criteria:

avoiding the use of formaldehyde cyanohydrin;

avoiding the dimerisation side reaction;

obtaining the required product directly in high yield and with high purity.

Therefore the present invention provides a process for preparing a compound of formula (I):

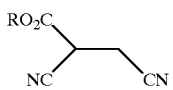

I wherein

R represents straight- or branched- chain alkyl having up to 18 carbon atoms; or a salt thereof;

which comprises the reaction of a cyanoacetate of formula (II):

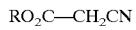

RO$_2$C—CH$_2$CN    II wherein R is as defined above, with a cyanide salt and formaldehyde or a source thereof.

Preferably R represents straight- or branched-chain alkyl having from 1 to 6 carbon atoms and most preferably R represents ethyl.

Suitable salts of cyanide include metal salts and organic salts (e.g. tetra-alkylammonium cyanides such as tetrabutylammonium cyanide). Preferably the cyanoacetate of formula (II) reacts with an alkali or alkaline earth metal cyanide salt, with alkali metal cyanide salts being especially suitable for use in the present invention, particularly potassium cyanide or sodium cyanide. The product may conveniently be isolated as the alkaline earth metal or alkali metal salt. Alternatively, the reaction mixture is acidified, for example with a mineral acid such as sulphuric acid or hydrochloric acid, to give the compound of formula (I). Where a compound of formula (I) above is desired (rather than a salt thereof) high yields are generally obtained when the reaction mixture is acidified without the addition of water. Whilst formaldehyde itself can be used in the reaction it is more convenient to use the polymerised form known as paraformaldehyde [(HCOH)$_n$], available for example from Aldrich Chemical Company.

The reaction is generally performed using about 1 molar equivalent of a compound of formula (II); about 0.95 to 1.0 molar equivalents of cyanide salt, and about 1 molar equivalent of formaldehyde compound (based on the formaldehyde content).

The reaction may be carried out in the presence of a solvent. Preferably, the reaction is performed in a solvent medium which is usually an alcoholic medium or dimethyl formamide (DMF), N-methyl pyrrolidone (NMP), dioxan, tetrahydrofuran (THF) or dimethoxyethane. Especially preferred solvents are C$_1$–C$_6$ alcohols such as methanol or, most preferably, anhydrous ethanol. Although the temperature of the reaction is not critical the reaction will normally be performed from about 0 to about 120° C. or at the reflux temperature of the solvent. Generally best results are obtained by introducing the formaldehyde source after the other reactants have been combined.

The reaction generally takes place under substantially anhydrous conditions (it being understood that the reaction proceeds with the formation of one equivalent of water), as in the event of prolonged exposure to aqueous conditions, there is a risk that the ester group of the compound of formula (I) will undergo hydrolysis (due to the basic conditions arising during the reaction) to the corresponding acid of formula (I) (in which R is replaced by hydrogen) and subsequently undergo decarboxylation to give 1,2-dicyanoethane.

The compound of formula (I) is useful in the preparation of pesticidally active compounds, for example as described in European Patent Publication Nos. 0295117 and 0234119, and WO93/06089.

In particular, the process of the invention may form part of an in situ preparation of another pesticidal intermediate and in a further aspect the invention provides a process for the preparation of a compound of formula (III):

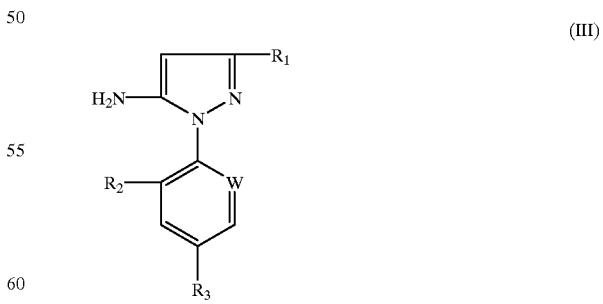

(III)

wherein R$_1$ is cyano; W is nitrogen or —CR$_4$; R$_2$ and R$_4$ independently represent halogen; and R$_3$ represents halogen, haloalkyl (preferably trifluoromethyl), haloalkoxy (preferably trifluoromethoxy) or —SF$_5$; which process comprises:

(a) reacting a cyanoacetate of formula (II) as defined above, with a cyanide salt and formaldehyde or a source thereof, to give a compound of formula (I) as defined above; and (b) reacting the compound of formula (I) thus obtained with the diazonium salt of a compound of formula (IV):

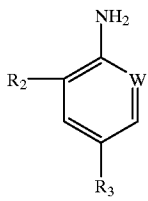

(IV)

wherein W, $R_2$ and $R_3$ are as defined above, to give a compound of formula (V):

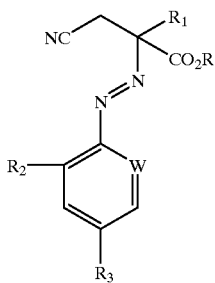

(V)

wherein W, R, $R_1$, $R_2$ and $R_3$ are as defined above, followed by the cyclisation of said compound of formula (V).

Compounds of formula (V) above possess a chiral centre giving rise to different enantiomers, and also may exist as different geometric isomers or mixtures thereof. All such forms are embraced by the present invention. In this process, the product of reaction step (a) is generally acidified with an alcoholic solution of a mineral acid, preferably an ethanolic solution of hydrogen chloride. This also ensures that any acid by-product of the reaction step (a) (leading to the corresponding compound of formula (I) in which R is replaced by hydrogen) is re-esterified. For these reasons it is also preferred that in this process, reaction step (a) takes place under substantially anhydrous conditions.

Reaction step (b) is generally performed in the presence of an inert solvent, for example water, acetonitrile, dichloromethane or DMF, or more preferably an alcoholic solvent (e.g. methanol or ethanol) and is optionally buffered (e.g. with sodium acetate). The diazonium salt of a compound of formula (IV) may be prepared using diazotising agents known in the literature and is conveniently prepared with a molar equivalent of sodium nitrite and a mineral acid (e.g. hydrochloric or sulphuric acid), at a temperature of from about −10° C. to about 50° C., more preferably from about 0° C. to about 5° C. The diazonium salt of the compound of formula (IV) is generally prepared in situ as solvents such as alcohols tend to reduce diazonium salts quickly. In the present reaction, the reaction of the diazonium salt of the compound of formula (IV) to give a compound of formula (V) above generally occurs faster than the reduction of the diazonium salt.

Subsequent hydrolysis, preferably using mild conditions with a base such as aqueous sodium hydroxide, sodium carbonate or ammonia, may be necessary to effect the cyclisation of the compound of formula (V) to a compound of formula (III).

The molar ratio of the compounds of formula (II):(IV) is generally from about 1.5:1 to about 1:4, preferably from about 1.3:1 to about 1:1, more preferably about 1.1:1.

Compounds of formula (III) and (IV) above are described in the literature, for example see EP-Al-0295117. Compounds of formula (V) above are novel and thus constitute a further feature of the present invention.

The following non-limiting examples illustrate the invention.

EXAMPLE 1

Preparation of ethyl 2,3-dicyanopropionate.

Potassium cyanide (13.0 g, 0.2M) was stirred in absolute ethanol and ethyl cyanoacetate (22.6 g, 0.2M) and paraformaldehyde (6.0 g, 0.2m) were added at ambient temperature. After 5 minutes the white suspension was heated under reflux conditions for 12 minutes, and the orange solution was evaporated to dryness in vacuo at below 25° C. to give a buff solid. The solid (the potassium salt) was dissolved in water (400 ml), acidified to pH 5 with 2M hydrochloric acid solution, giving a red oil. This mixture was extracted with dichloromethane and the extracts dried and evaporated to dryness in vacuo to give the title compound as a red oil (23.5 g), $^1$H NMR (CDCl$_3$) d 4.3 (2H, q), 3.95 (1H, t), 3.0 (2H, d), 1.35 (3H, t); identical with an authentic sample. Distilled material had b.p. 132–136° C. at 0.5mmHg. Yield : 77%.

Comparative Example According to J. Chem. Soc. 89, 1460 (1906)

A solution of sodium ethoxide [prepared from sodium (25.2 g, 1.15M) and absolute ethanol (650 ml)] was stirred under an inert atmosphere and treated with ethyl cyanoacetate (127.7 ml 1.2M) over 20 minutes. The solution was cooled to below 10° C. and then added slowly to a solution of formaldehyde cyanohydrin (freshly prepared, 70 g, 0.2M) in absolute ethanol (200 ml) at 50° C. over 55 minutes. After standing overnight the mixture was poured into ice-water (1L) and acidified to pH 1–2 with concentrated hydrochloric acid. This was extracted into dichloromethane, dried over anhydrous magnesium sulphate and evaporated to give a dark orange oil (150.6 g). This was distilled in vacuo collecting the title compound (73.6 g) as a colourless oil, b.p. 144–148° C./1 mbar. Yield: 40%

The superiority of the process of the invention is thus clearly demonstrated over this prior art.

EXAMPLE 2

Process for the preparation of 5-amino-3-cyano-1-(2,6-dichloro-4-trifluoromethyl-phenyl)pyrazole.

Sodium cyanide (20 g, 0.408M) and ethyl cyanoacetate (46 g, 0.408M) were dissolved in absolute ethanol (300 ml) under an inert atmosphere. Paraformaldehyde (12.2 g, 0.408M) was added, producing an exotherm, and the temperature was maintained below 50° C. The reaction mixture was then stirred at ambient temperature for between 5 and 7 hours, cooled to between 0 and 5° C., and an ethanolic solution containing hydrogen chloride (0.45M) was added, maintaining the temperature below 5° C. The reaction mixture was left overnight and 111 ml of a solution of hydrochloric acid (0.73M) in ethanol was added to the suspension thus obtained at about 5° C. 2,6-Dichloro-4-trifluoromethylaniline (84.44 g, 0.367M) was added at this temperature followed by sodium nitrite (35.84 g, 0.514M) resulting in the formation of ethyl 2,3-dicyano-2-[2,6- dichloro-4-trifluoromethylphenyl)azo]propionate, which may be isolated by column chromatography, eluting with a pentane/ether solution and/or reverse phase chromatography with an acetonitrile-water solution; or by removing the ethanol by distillation, dissolving the reaction mixture in toluene, washing the toluene solution with water and evaporating the toluene to dryness. $^1$H NMR (CDCl$_3$) 1.37(t,3H), 3.55(s,2H), 4.43(q,2H), 7.65(s,2H).

Ammonia gas (9.6 g, 0.56M) was then bubbled into the reaction mixture at 0° C. The ethanol was evaporated from the reaction mixture under reduced pressure and the concentrated liquors were taken up into a mixture of toluene and ethyl acetate. This solution was washed with water and after concentration of the toluene phase at 80° C., the solution was cooled to give the title compound as a crystalline solid, and the liquors were then concentrated and cooled to give a second crop of recrystallised product, m.p. 141–142° C. (combined weight of title compound 87.54 g; yield based on aniline starting material=78%).

What is claimed is:

1. A process for preparing a compound of formula (I):

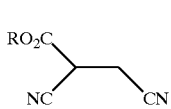
(I)

wherein
R represents straight- or branched-chain alkyl having from 1 to 18 carbon atoms,
or a salt thereof, which comprises a reacting a cyanoacetate of formula (II):

$RO_2C—CH_2CN$ (II)

wherein R is as defined above,
with a cyanide salt, and formaldehyde or a source of formaldehyde.

2. A process according to claim 1 in which the cyanide salt is an alkali or alkaline earth metal salt.

3. A process according to claim 2 wherein the cyanide salt is sodium or potassium cyanide.

4. A process according to claim 1, wherein R represents straight- or branched-chain alkyl having from 1 to 6 carbon atoms.

5. A process according to claim 1, wherein the compound of formula (II) is ethyl cyanoacetate.

6. A process according to claim 1, wherein the source of formaldehyde is paraformaldehyde.

7. A process according to claim 1, wherein the reaction is performed in presence of a solvent which is an alcoholic medium.

8. A process according to claim 1 wherein the reaction is carried out at a temperature from about 0° C. to about 120° C.

9. A process according to claim 1 in which the reaction is performed using about 1 molar equivalent of the compound of formula (II); about 0.95 to 1.0 molar equivalent of cyanide salt; and about 1 molar equivalent of formaldehyde compound.

10. A process according to claim 1 in which the reaction mixture is acidified after reacting the cyanoacetate of formula (II) with the cyanide salt and formaldehyde.

11. A process according to claim 1, in which the reaction is performed under substantially anhydrous conditions.

12. A compound of formula (V):

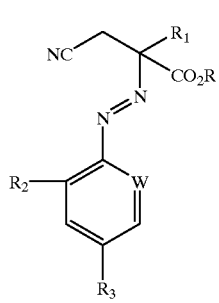
(V)

wherein R$_1$ is cyano; W is nitrogen or —CR4; R$_2$ and R$_4$ independently represent halogen; and R$_3$ represents halogen, haloalkyl, haloalkoxy or SF$_5$.

13. Ethyl 2,3-dicyano-2-[(2,6-dichloro-4-trifluoromethylphenyl)azo]propionate.

14. A process according to claim 2 wherein R represents straight- or branched-chain alkyl having from 1 to 6 carbon atoms.

15. A process according to claim 3 wherein R represents straight- or branched-chain alkyl having from 1 to 6 carbon atoms.

16. A process according to claim 2 wherein the compound of formula (II) is ethyl cyanoacetate.

17. A process according to claim 3 wherein the compound of formula (II) is ethyl cyanoacetate.

18. A process according to claim 4 wherein the compound of formula (II) is ethyl cyanoacetate.

19. A process according to claim 2 wherein the source of formaldehyde is paraformaldehyde.

20. A process according to claim 3 wherein the source of formaldehyde is paraformaldehyde.

21. A process according to claim 4 wherein the source of formaldehyde is paraformaldehyde.

22. A process according to claim 5 wherein the source of formaldehyde is paraformaldehyde.

23. A process according to claim 14 wherein the source of formaldehyde is paraformaldehyde.

24. A process according to claim 15 wherein the source of formaldehyde is paraformaldehyde.

25. A process according to claim 16 wherein the source of formaldehyde is paraformaldehyde.

26. A process according to claim 17 wherein the source of formaldehyde is paraformaldehyde.

27. A process according to claim 18 wherein the source of formaldehyde is paraformaldehyde.

28. A process for the preparation of a compound of formula (III):

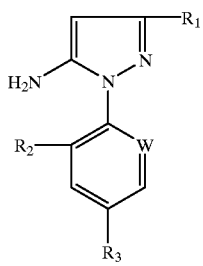
(III)

wherein R$_1$ is cyano; W is nitrogen or —CR$_4$; R$_2$ and R$_4$ independently represent halogen; and R$_3$ represents halogen, haloalkyl, haloalkoxy or SF$_5$; said process comprising:

(a) reacting a cyanoacetate of formula (II):

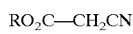 (II)

wherein R represents straight- or branched-chain alkyl having from 1 to 18 carbon atoms, with a cyanide salt, and formaldehyde or a source of formaldehyde, to afford a compound of formula (I):

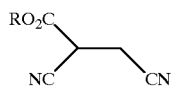 (I)

wherein R is as defined above; and (b) reacting the resultant compound of formula (I) with the diazonium salt of a compound of formula (IV):

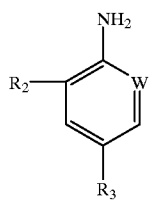 (IV)

wherein W, $R_2$ and $R_3$ are as defined above, to afford a compound of formula (V):

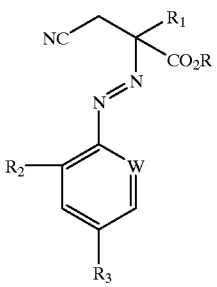 (V)

wherein W, R, $R_1$, $R_2$ and $R_3$ are as defined above, followed by cyclizing the resultant compound of formula (V) to produce the desired compound at formula (III).

29. A process according to claim 28 in which the product of reaction step (a) is treated with an alcoholic solution of an acid.

30. A process according to claim 29 in which the product of reaction step (a) is treated with an alcoholic solution of a mineral acid.

31. A process according to claim 28 in which the molar ratio of the compound of formula (II) to the compound of formula (IV) is from about 1.5:1 to about 1:4.

32. A process according to claim 31 in which the molar ratio of the compound of formula (II) to the compound of formula (IV) is from about 1.3:1 to about 1:1.

33. A process according to claim 28 in which reaction step (a) is performed under substantially anhydrous conditions.

34. A process according to claim 29 in which reaction step (a) is performed under substantially anhydrous conditions.

35. A process according to claim 30 in which reaction step (a) is performed under substantially anhydrous conditions.

36. A process according to claim 31 in which reaction step (a) is performed under substantially anhydrous conditions.

37. A process according to claim 32 in which reaction step (a) is performed under substantially anhydrous conditions.

38. A process according to claim 28 in which the cyclization is effected by hydrolysis of the compound of formula (V).

* * * * *